(12) United States Patent
Ogawa

(10) Patent No.: US 6,945,931 B2
(45) Date of Patent: Sep. 20, 2005

(54) ENDOSCOPE SYSTEM FOR MEASURING THE AREA OF A MISSING PORTION

(75) Inventor: Kiyotomi Ogawa, Tokyo (JP)

(73) Assignee: Olympus Corporation (JP)

( * ) Notice: Subject to any disclaimer, the term of this patent is extended or adjusted under 35 U.S.C. 154(b) by 224 days.

(21) Appl. No.: 10/611,733

(22) Filed: Jul. 1, 2003

(65) Prior Publication Data

US 2004/0054256 A1 Mar. 18, 2004

(30) Foreign Application Priority Data

Jul. 1, 2002 (JP) ........................................ 2002-192448

(51) Int. Cl.[7] ................................................ A61B 1/04

(52) U.S. Cl. ........................................ 600/118; 600/109

(58) Field of Search ................................ 600/109, 160, 600/117–118; 356/237.1, 240.1, 241.1, 237.2, 237.5; 382/108

(56) References Cited

U.S. PATENT DOCUMENTS 5,966,677 A * 10/1999 Fiekowsky .................... 702/95
6,063,023 A    5/2000 Sakiyama et al.
6,459,481 B1 * 10/2002 Schaack .................. 356/241.1

FOREIGN PATENT DOCUMENTS

JP    2001-275934    10/2001

* cited by examiner

Primary Examiner—John Leubecker
Assistant Examiner—Philip R Smith
(74) Attorney, Agent, or Firm—Ostrolenk, Faber, Gerb & Soffen, LLP

(57) ABSTRACT

A measurement endoscope system comprises an electronic endoscope, an image processing unit, a control device, a display device, a first reference line designation block, a first reference plane designation block, a contour border designation block, and an arithmetic and logic block. The electronic endoscope has an imaging unit. The present invention relates to a measurement endoscope system that measures the area of a missing portion of an object matter, or more particularly, the area of a missing portion of an edge of an object matter.

8 Claims, 15 Drawing Sheets

FIG.7A FIG.7B
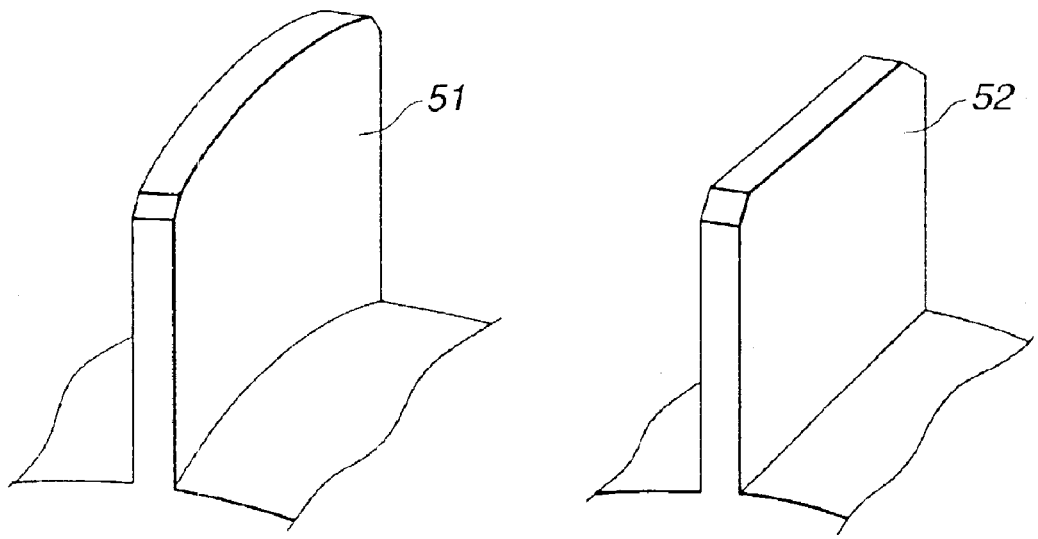
FIG.8
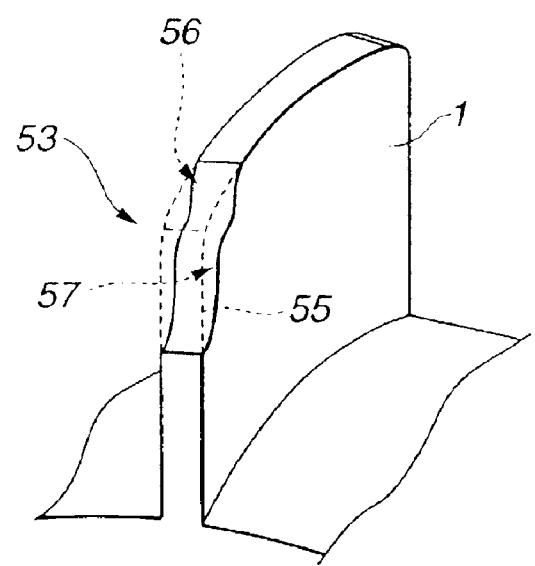

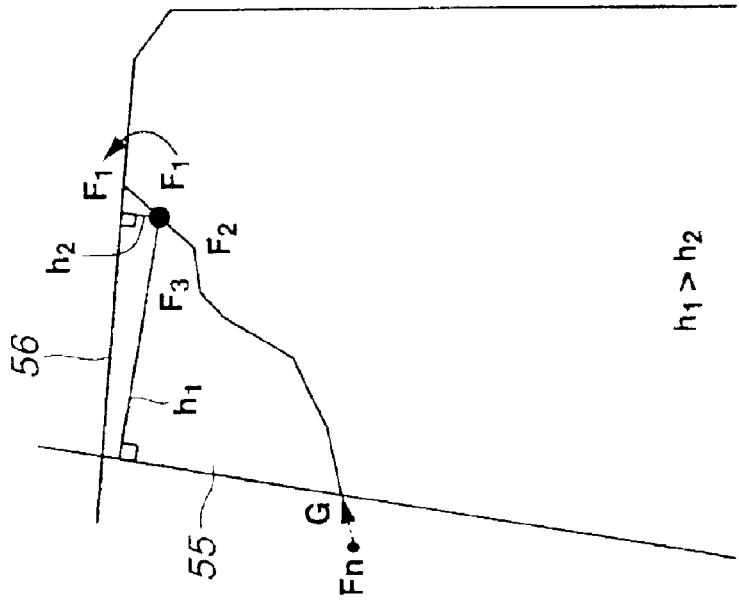
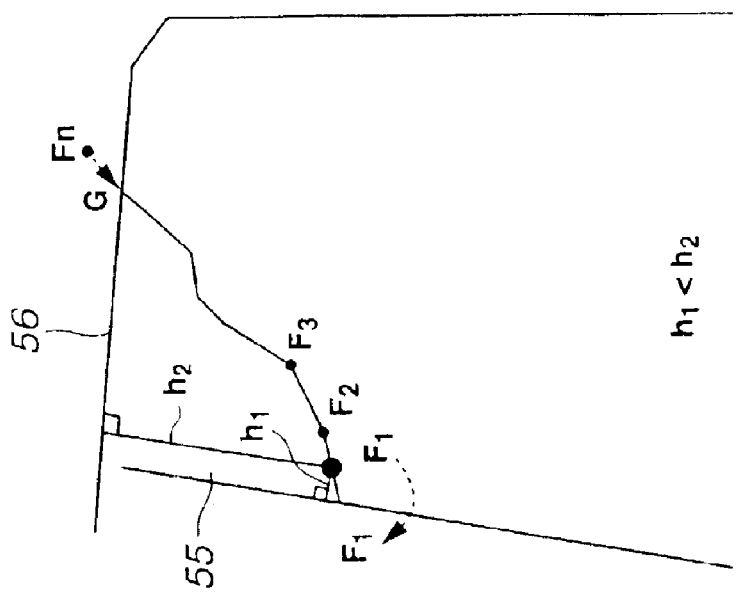

ENDOSCOPE SYSTEM FOR MEASURING THE AREA OF A MISSING PORTION

This application claims the benefit of Japanese Application No. 2002-192448 filed on Jul. 1, 2002, the contents of which are incorporated by this reference.

BACKGROUND OF THE INVENTION

1. Field of the Invention

The present invention relates to a measurement endoscope system that measures the area of a missing portion of an object matter, or more particularly, the area of a missing portion of an edge of an object matter.

2. Description of the Related Art

In recent years, endoscopes having an elongated insertion unit thereof inserted into a body cavity for the purpose of observing an intracavitary organ or the like or of performing various kinds of cures or treatments using, if necessary, a treatment instrument lying through a treatment instrument channel have been widely adopted. In the field of industries, endoscopes for industrial use have been widely used to observe or inspect the interior of a boiler, a turbine, an engine, or a chemical plant to see if the interior is flawed or corroded.

The endoscopes for the above usage include an electronic endoscope (hereinafter, an endoscope) having an imaging device such as a CCD, which photoelectrically converts an optical image into an image signal, incorporated in the distal section of the insertion unit. In the endoscope, an image processing unit produces a video signal from the image signal representing a view image converged on the imaging device. The video signal is transmitted to a monitor, whereby an endoscopic image is displayed on the screen of the monitor for observation.

In particular, the endoscope for industrial use may be requested to measure an object part so as to assist in inspecting an object matter in details. In order to satisfy the request, various types of measuring means capable of measuring an object part using an endoscope have been proposed in the past.

For example, Japanese Unexamined Patent Application Publication No. 2001-275934 describes a measurement endoscope system that enjoys the improved maneuverability for measurement and contributes to improvement of efficiency in inspection by performing a measurement process associated with an attached optical adapter.

In the measurement endoscope system, when an optical adapter is selected on the screen of a display device, a measurement process associated with the optical adapter is automatically selected. In order to perform measurement, a measurement execution switch located on the operation unit of an endoscope is pressed. Consequently, measurement is executed according to the measurement process associated with the optical adapter. The measurement endoscope system can measure the length of, for example, a crack occurring in an object matter or the area of a hole formed in a corroded portion of the surface of the object matter.

The area of the hole is measured as shown in FIG. 1. First, a plurality of points, for example, points A to G are designated on the outline of an image of the hole 101 displayed on the screen 100 of a display device. Segments shown by alternate long and short lines are successively drawn to link the respective adjoining ones of the points. Thereafter, a portion defined with the segments is closed at last, and the area of the defined portion is calculated.

To be more specific, the points A to G are successively designated, and a point H is designated so that a segment linking the point A and the point H will intersect the segment AB drawn first to close the defined portion. During the designation of the point H, a measurement program adopts a point closest to the point H (point A in the drawing) as a final point so as to close the defined portion. Thereafter, the closed graphic is replaced with a manifold of triangles ($\triangle$ABC, $\triangle$ACD, $\triangle$ADE, $\triangle$AEF, and $\triangle$AFG). The areas of the triangles are then calculated. Finally, the areas are summated in order to work out the area of the hole.

SUMMARY OF THE INVENTION

A measurement endoscope system comprises an electronic endoscope, an image processing unit, a control device, a display device, a first reference line designating means, a first reference plane designating means, a contour designating means, and an arithmetic and logic means. The electronic endoscope includes an imaging unit. The image processing unit receives an imaging signal from the imaging unit so as to produce a video signal. The control device includes at least a control unit that has a measurement processing block which performs measurement on the basis of an image signal produced by the image processing unit. The display device receives the video signal in response to a direction given by the control unit included in the control device, and displays an image represented by the video signal. The first reference line designating means includes a missing-edge portion measuring means that measures the area of a missing portion of an edge of an object matter and that is included in the measurement processing block included in the control unit. The first reference line designating means designates a first reference line that corresponds to a side surface of an object part which the periphery of the missing edge portion used to contain. The first reference plane designating means designates a first reference plane that corresponds to the top of the object part the periphery of the missing edge portion used to contain and that intersects the first reference line, which is designated by the first reference line designating means, at one point. The contour designating means designates any points on the border of the missing edge portion so as to form a missing-contour border. The arithmetic and logic means calculates the area of a field that is formed by moving the missing-contour border designated by the contour designating means up to the first reference plane in a direction parallel to the direction of the first reference line, and that is defined with the missing-contour border, first reference line, and first reference plane.

The above and other objects of the present invention, and the features and advantages thereof will be more clearly understood from the following description made with reference to the accompanying drawings.

BRIEF DESCRIPTION OF THE DRAWINGS

FIG. 7A shows a curved blade that is a curved type turbine blade included in a turbojet engine;

FIG. 7B shows a block blade that is a rectangular parallelepiped type turbine blade included in a turbojet engine;

FIG. 8 is an explanatory diagram concerning a first reference line, a first reference plane, and a missing-contour border which relate to a missing edge portion of a curved blade;

FIG. 17A is an explanatory diagram concerning a procedure of determining a contour border from the first-reference line side, and a procedure of determining a designation start point;

FIG. 17B is an explanatory diagram concerning a procedure of determining a contour border from the first-reference plane side, and a procedure of determining a designation start point;

DESCRIPTION OF THE PREFERRED EMBODIMENTS

Figure 1:
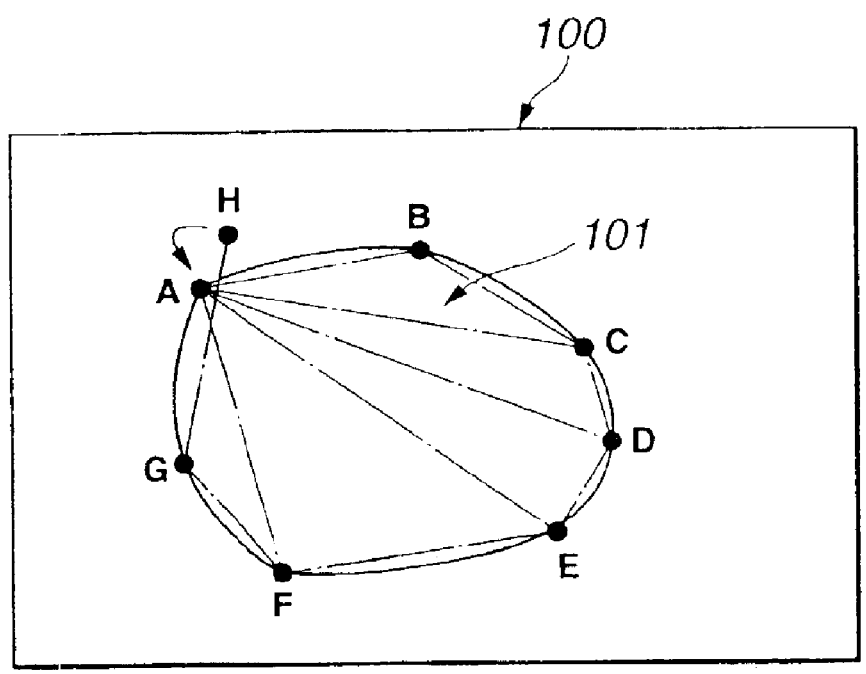
FIG. 1 is an explanatory diagram concerning a process of measuring the area of a hole using a measurement program installed in a conventional measurement endoscope system.

Referring to the drawings, a measurement endoscope system will be described below.

Figure 2:
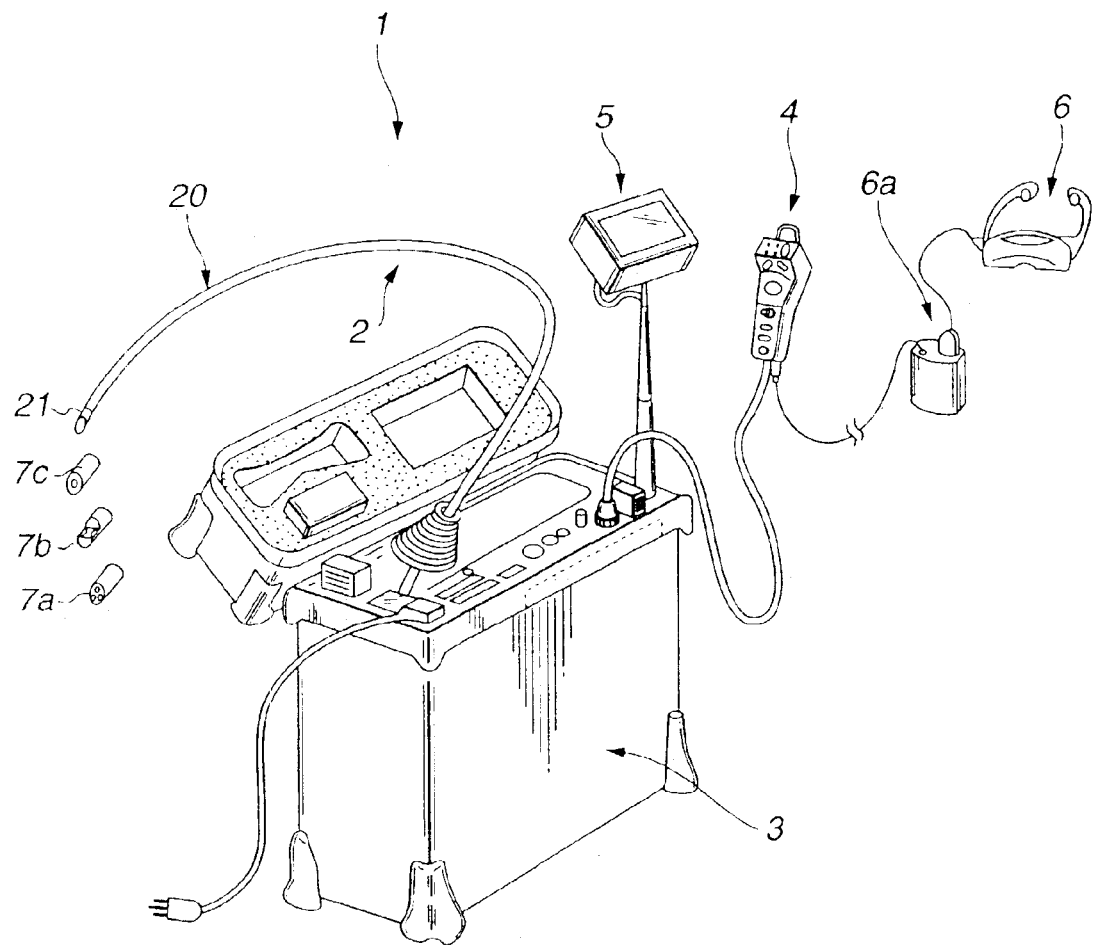
FIG. 2 is an explanatory diagram showing a measurement endoscope system.

As shown in FIG. 2, a measurement endoscope system 1 mainly comprises an endoscope 2, a controller 3 that is a control device, a remote controller 4, a liquid crystal monitor (hereinafter LCD) 5 that is a display device, and a face-mounted display (hereinafter FMD) 6.

The endoscope 2 includes an elongated insertion unit 20. The controller 3 includes a storage chamber in which the insertion unit is stored. The remote controller 4 is used to operate the entire system so as to execute various necessary action control sequences. An endoscopic image and the contents of operation control (for example, a processing menu to be described later) are displayed on the LCD 5. The FMD 6 permits viewing of a normal endoscopic image or permits quasi stereoscopic viewing of the endoscopic image. The FMD 6 has an FMD adapter 6a that transmits image data to the FMD 6.

The insertion unit 20 has a hard distal section 21, a bending section 22 that can be bent, for example, vertically and horizontally, and a flexible tube 23, which has flexibility, concatenated in that order from the distal end thereof. Various types of optical adapters including stereoscopic optical adapters 7a and 7b that offer two observational fields of view and a normal observation optical adapter 7c that offers one observational field of view can be freely detachably attached to the distal section 21, for example, can be screwed to the distal section so that they can be unscrewed freely.

Figure 3:
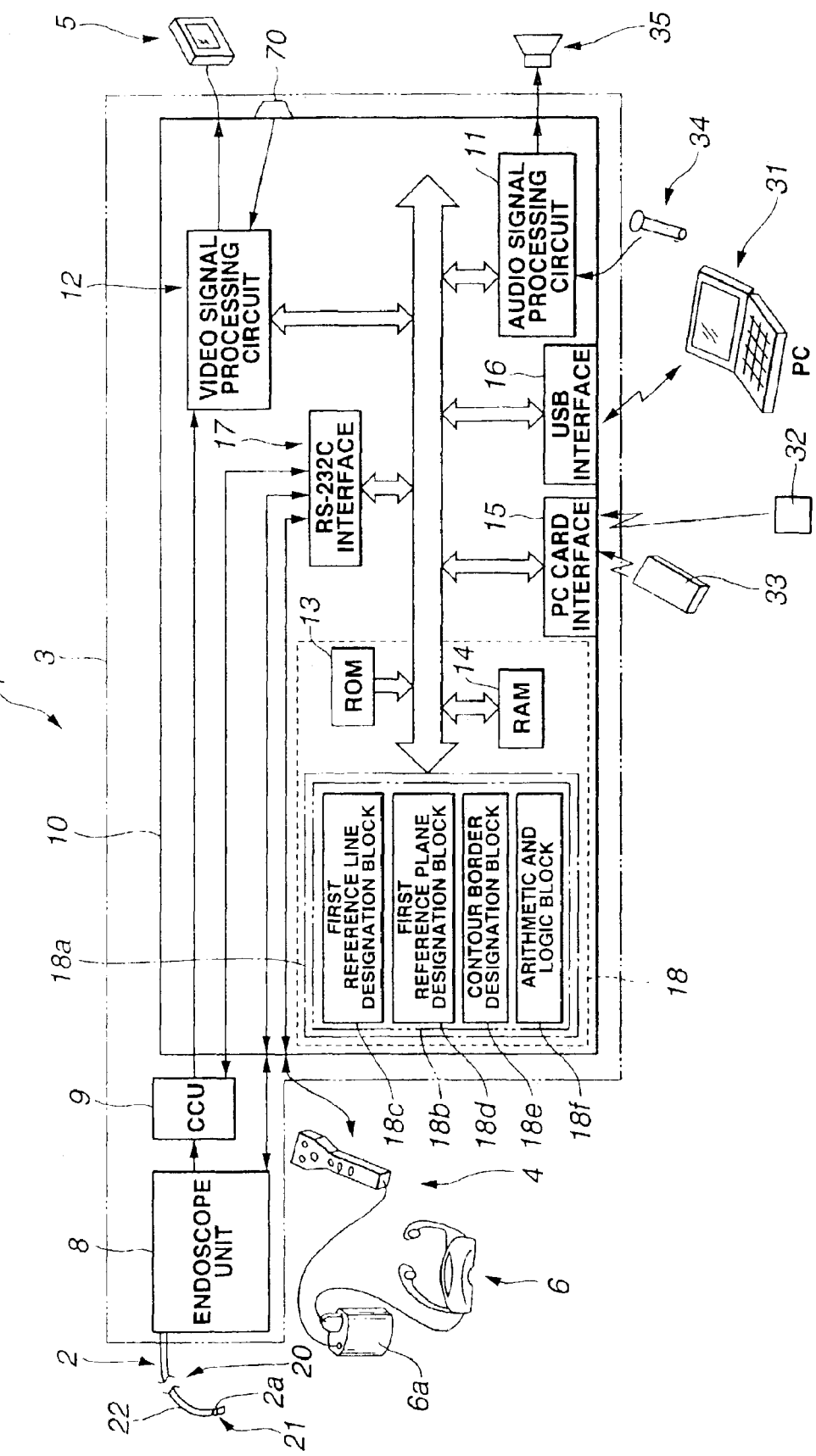
FIG. 3 is a block diagram showing the configuration of the measurement endoscope system.

As shown in FIG. 3, the controller 3 includes an endoscope unit 8, a camera control unit 9 (hereinafter CCU) that is an image processing unit, and a control unit 10. The proximal end of the insertion unit 20 is coupled to the endoscope unit 8.

The endoscope unit 8 includes a light source device (not shown) that supplies illumination light necessary for observation, and a bending device (not shown) that bends the bending section 22 of the insertion unit 20.

The CCU 9 receives an imaging signal sent from a solid-state imaging device 2a incorporated in the distal section 21 of the insertion unit 20. The imaging signal is converted into a video signal, for example, an NTSC signal within the CCU 9, and transmitted to the control unit 10.

The control unit 10 includes an audio signal processing circuit 11, a video signal processing circuit 12 that receives the video signal, a ROM 13, a RAM 14, a PC card interface 15, a USB interface 16, an RS-232C interface 17, and a CPU 18.

The CPU 18 implements various features according to a main program, controls actions, and includes a measurement processing block 18a that performs measurement processing. The measurement processing block 18a includes a missing-edge portion measurement block 18b that is a missing-edge portion measuring means for measuring the area of a missing portion of an edge of an object matter as described later.

The CCU 9, the endoscope unit 8, and the remote controller 4 that is used to control the CCU 9 and endoscope unit 8 and to direct them to act are connected to the RS-232C interface 17. Consequently, when the remote controller 4 is handled, a required control signal is communicated to the CCU 9 and endoscope unit 8 according to the handling.

The USB interface 16 is an interface via which the controller 3 and a personal computer 31 are electrically connected to each other. When the controller 3 and personal computer 31 are connected to each other via the USB interface 16, various directions can be controlled and data can be transmitted or received. In other words, the personal computer 31 can be used to direct display of an endoscope image or control the direction of image processing given during measurement. Consequently, control information or data required for various kinds of processing can be transmitted or received between the controller 3 and personal computer 31.

A so-called memory card that is a recording medium, such as, a PCMCIA memory card 32 or a compact flash® memory card 33 can be loaded in the PC card interface 15 so that it can be unloaded freely.

When the memory card is loaded in the PC card interface 15, control processing information, image information, or any other data can be fetched from the memory card under the control of the CPU 18. Otherwise, control processing information, image information, or any other data can be recorded in the memory card.

The video signal processing circuit 12 performs the processing required to display a synthetic image, which is produced by synthesizing an endoscopic image sent from the CCU 9 with an operation menu that is a graphic, on the LCD 5. Specifically, the video signal processing circuit 12 synthesizes a video signal sent from the CCU 9 with a display signal representing an operation menu and being produced under the control of the CPU 18, and performs the processing required to display an image on the screen of the LCD 5. Thereafter, the video signal processing circuit 12 transmits the resultant video signal to the LCD 5. Incidentally, the video signal processing circuit 12 can perform the processing for solely displaying an endoscopic image or an operation menu graphic.

Consequently, an endoscopic image, an operation menu graphic, and a synthetic image of the endoscopic image and operation menu graphic are displayed on the screen of the LCD 5.

Various audio signals are transferred to the audio signal processing circuit 11. The audio signal processing circuit 11 performs amplification and other processing required to regenerate received audio signals, and transmits the resultant signals to a loudspeaker 35. Consequently, sounds are radiated from the loudspeaker 35.

The audio signals are produced by collecting sounds using a microphone 34 and recorded in the memory card or any other recording medium, regenerated from the memory card or any other recording medium, or produced by the CPU 18.

The CPU 18 runs a program stored in the ROM 13 to control various circuits so that indented processing will be carried out, and thus controls the entire system.

Figure 4:
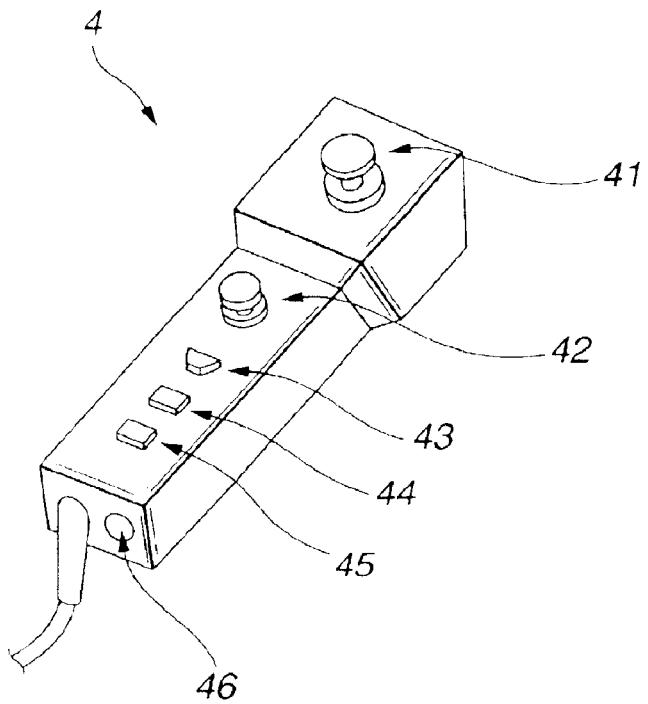
FIG. 4 is an explanatory diagram showing a remote controller.

As shown in FIG. 4, a joystick 41, a lever switch 42, a Freeze switch 43, a Store switch 44, and a measurement execution switch 45 are located on one side of the remote controller 4.

The joystick 41 is a switch for use in directing the bending section 22 to bend. By tilting the joystick 41, the bending section 22 is bent by an angle, by which the joystick 41 is tilted, in the direction in which the joystick is tilted.

The lever switch 42 is a switch for use in moving a pointer to handle various menus displayed as graphics or perform measurement. The lever switch 42 has substantially the same structure as the joystick 41.

The Freeze switch 43 is a switch relevant to display on the LCD 5.

The Store switch 44 is a switch for use in recording a still image, which is displayed by pressing the Freeze switch 43, in the memory card.

The measurement execution switch 45 is a switch for use in running measurement software.

The Freeze switch 43, Store switch 44, and measurement execution switch 45 are formed with, for example, push-button switches that are turned on or off when pressed.

Reference numeral 46 denotes a connector into which an electric cable extending from the FMD adapter 7 is plugged. When the electric cable is plugged into the connector 46, the FMD 6 permits stereoscopic viewing.

Now, an example of typical control actions to be performed by the CPU 18 included in the measurement endoscope system 1 of the present embodiment will be described with reference to FIG. 5A and FIG. 5B.

When the power supply of the measurement endoscope system 1 is turned on, the CPU 18 runs a major program. A standby state is established due to a loop composed of decision-making of steps S100, S101, S102, S103, and S109 described in FIG. 5A. Thereafter, when a function is designated at step S100, S101, or S102, processing for implementing each function is carried out. When measurement is designated at step S103, control is passed to step S104.

At the decision-making of step S103, it is decided whether an optical adapter to be attached to the distal section 21 of the endoscope 2 has been designated or whether an optical adapter should be attached to the distal section 21. When no optical adapter is designated, it is decided at step S109 whether processing is completed. When it is decided that processing is completed, the routine is terminated. Otherwise, control is returned to step S100.

On the other hand, when it is decided at step S103 that an optical adapter has been attached to the distal endoscope section 21 or an attached optical adapter has been designated, control is passed to step S104. Namely, when control is passed to the decision-making of step S104, a wait state is established for waiting until an entry is made to an optical adapter designation function.

Figure 6:
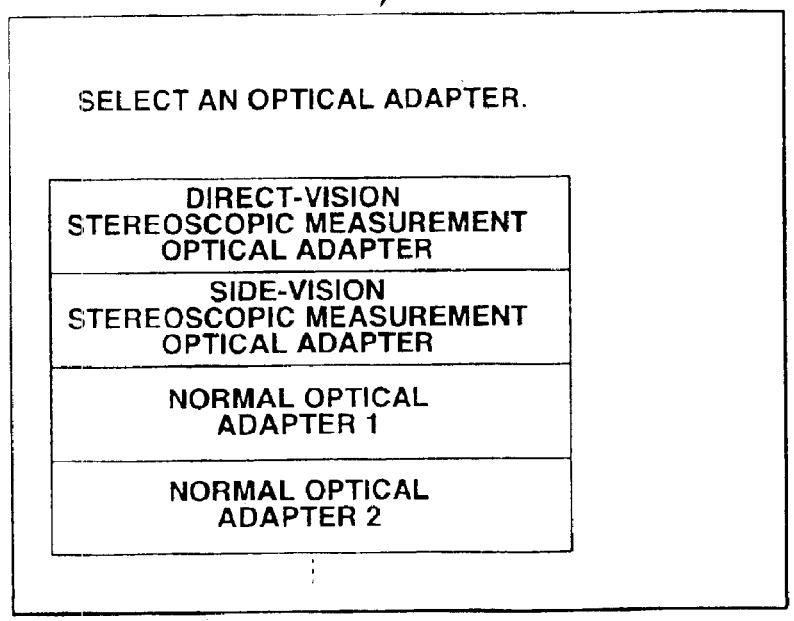
FIG. 6 is an explanatory diagram showing an optical adapter selection screen image.

For example, when any of the optical adapters is attached to the distal section 21, the CPU 18 calls the optical adapter designation function and passes control to step S104. Consequently, a display signal representing an optical adapter selection screen image is produced using the optical adapter designation function and transferred to the video signal processing circuit 12. Eventually, an optical adapter selection screen image 5A like the one shown in FIG. 6 is displayed on the LCD 14. A user designates an adapter by selecting any of the items from the selection screen image.

Thereafter, the CPU 18 verifies at the decision-making of the next step S105 whether the optical adapter the user has selected is a normal optical adapter. When the optical adapter is the normal optical adapter, a comparative measurement flag is set to 1 at the next step S106. Moreover, a stereoscopic measurement flag is cleared. Control is then passed to step S107. In contrast, when the optical adapter is not the normal optical adapter, control is passed to step S107.

At step S107, the CPU 18 verifies whether the optical adapter the user has selected is a stereoscopic measurement adapter. When the optical adapter is the stereoscopic measurement adapter, the comparative measurement flag is cleared at the next step S108. Moreover, the stereoscopic measurement flag is set to 1. The measurement endoscope system 1 is controlled to enter a use standby state and stays in the standby state until the user presses the measurement execution switch 45 on the remote controller 4. On the other hand, when the optical adapter is not the stereoscopic measurement adapter, the measurement endoscope system is controlled to enter the standby state.

Figure 5A:
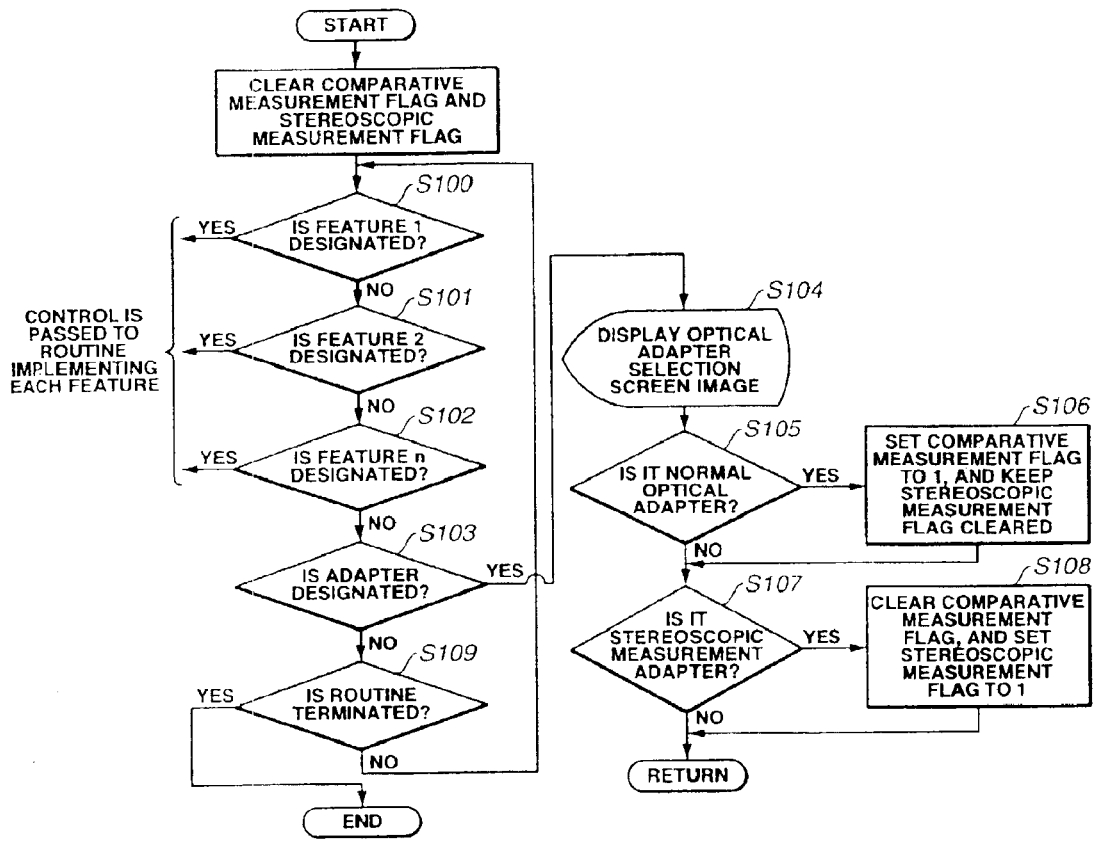
FIG. 5A is a flowchart describing an example of control actions performed by a CPU.
Figure 5B:
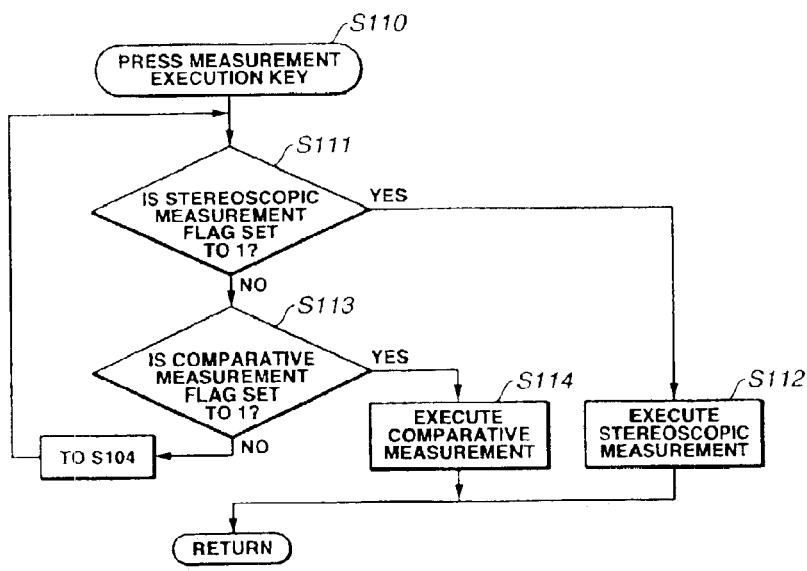
FIG. 5B is a flowchart describing measurement execution control.

When the user presses the measurement execution switch 45 on the remote controller 4, the CPU 18 runs a program of a routine described in FIG. 5B.

At step S110, it is detected whether the measurement execution switch (measurement execution key in the drawing) 45 is pressed. At the next step S111, it is verified whether the stereoscopic measurement flag is set to 1. When the stereoscopic measurement flag is set to 1, it is decided that stereoscopic measurement has been designated. Control is then passed to step S112, and control is extended as mentioned previously so that stereoscopic measurement will be executed. When the stereoscopic measurement is completed, the measurement endoscope system 1 is brought to the standby state so that it will get ready for display of the result of the measurement or for another measurement.

On the other hand, when it is decided at step S111 that the stereoscopic measurement flag is not set to 1, control is passed to the next step S113. It is then verified whether the comparative measurement flag is set to 1. When the comparative measurement flag is set to 1, it is decided that normal comparative measurement has been designated, and control is passed to the next step S114. Control is then extended as mentioned above in order to execute comparative measurement. When the comparative measurement is completed, the measurement endoscope system 1 is as mentioned above brought to the standby state so that it will get ready for display of the result of the measurement or for another measurement.

When it is verified at step S113 that the comparative measurement flag is not set to 1, control is passed to step S111 or step S103 included in the routine described in FIG. 5A. Control is thus extended so that the settings needed to execute measurement will be checked again.

According to the present embodiment, when the measurement execution switch 45 on the remote controller 4 is turned on, a measurement program designated with the flags is run. In other words, when an inspector presses the measurement execution switch 45, a measurement process associated with an attached optical adapter is automatically executed.

Now, a description will be made of a case where the measurement endoscope system 1 having the foregoing components is used to measure the area of a missing portion of an edge of, for example, a turbine blade included in a turbojet engine.

Incidentally, the turbine blade to be included in a turbojet-engine is broadly classified into two types, that is, a curved type including a curved blade 51 like the one shown in FIG. 7A, and a rectangular parallelepiped type including a block blade 52 like the one shown in FIG. 7B. According to the present embodiment, the turbine blade included in the turbojet engine shall be of the curved type and be the curved blade 51.

The missing-edge portion measurement block 18b included in the measurement processing block 18a incorporated in the CPU 18 shown in FIG. 3 comprises a first reference line designation block 18c that is a first reference line designating means, a first reference plane designation block 18d that is a first reference plane designating block, a contour border designation block 18e that is a contour designating means, and an arithmetic and logic block 18f that is an arithmetic and logic means.

The first reference line designation block 18c designates a first reference line 55 that corresponds to a side surface of the curved blade 51 which the periphery of a missing edge portion 53 used to contain.

The first reference plane designation block 18d designates a first reference plane 56 that corresponds to the top of the curved blade which the periphery of the missing edge portion 53 used to contain and that intersects the first reference line 55, which is designated by the first reference line designation block 18c, at one point.

The contour border designation block 18e designates any points on the border of the missing edge portion 53 so as to determine a missing-contour border 57.

The arithmetic and logic block 18f moves the missing-contour border 57, which is designated by the contour border designation block 18e, in a direction parallel to the direction of the first reference line 55. The arithmetic and logic block 18f then determines points at which the missing-contour border 57 intersects the first reference plane 56, and calculates the area of a field defined with the missing-contour border 57, first reference line 55, and first reference plane 56.

When an inspector discovers the missing edge portion 53 during inspection of the turbine blade, the inspector turns on the measurement execution switch 45 on the remote controller 4.

Figure 9:
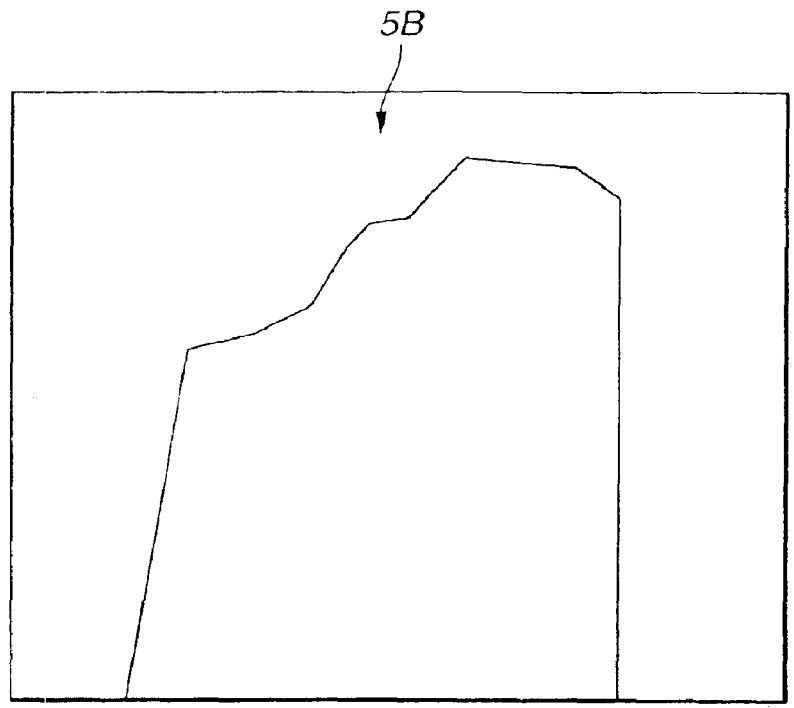
FIG. 9 shows an endoscopic image that renders a blade whose edge portion is missing and that is displayed on a screen.

An endoscopic image 5B of the turbine blade rendering the missing edge portion 53 is, as shown in FIG. 9, displayed on the screen of the LCD 14. This brings about an area-of-missing portion measurement start state.

When the endoscopic image 5B shown in FIG. 9 is displayed, first, the inspector performs a first procedure for determining the first reference line 55, a second procedure for determining the first reference plane 56 that intersects the first reference line 55, and a third procedure for determining the missing-contour border 57 for the purpose of calculating the area of the missing edge portion 53.

Figure 10:
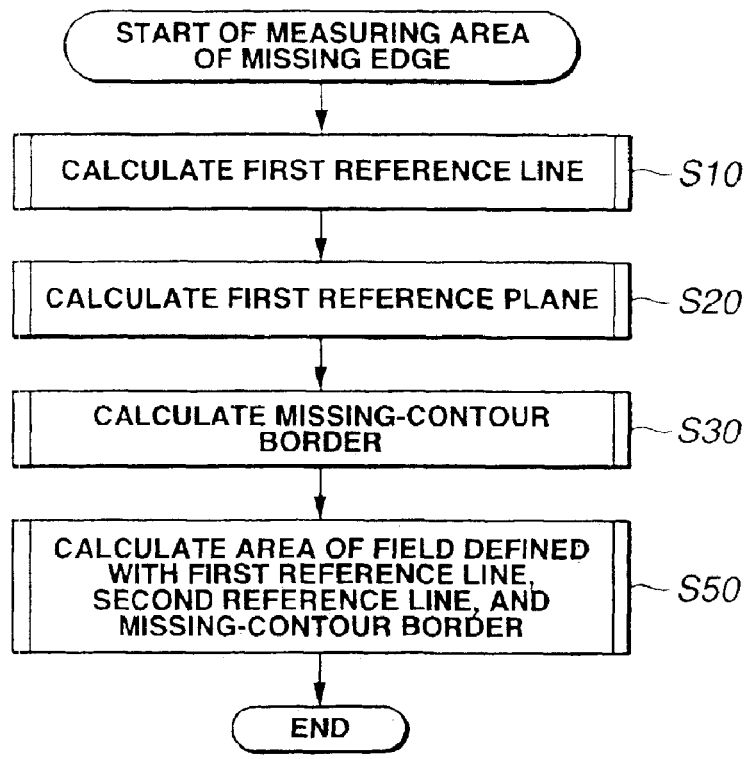
FIG. 10 is an explanatory diagram describing a processing flow of measuring the area of a missing edge portion.

Consequently, the missing-edge portion measurement block 18b incorporated in the CPU 18 performs determination of the first reference line of step S10 described in FIG. 10, determination of the first reference plane of step S20, determination of the missing-contour border of step S30, and calculation of the area of the missing edge portion 53 of step S50. The missing-edge portion measurement block 18b thus calculates the area of the missing edge portion 53.

Figure 11:
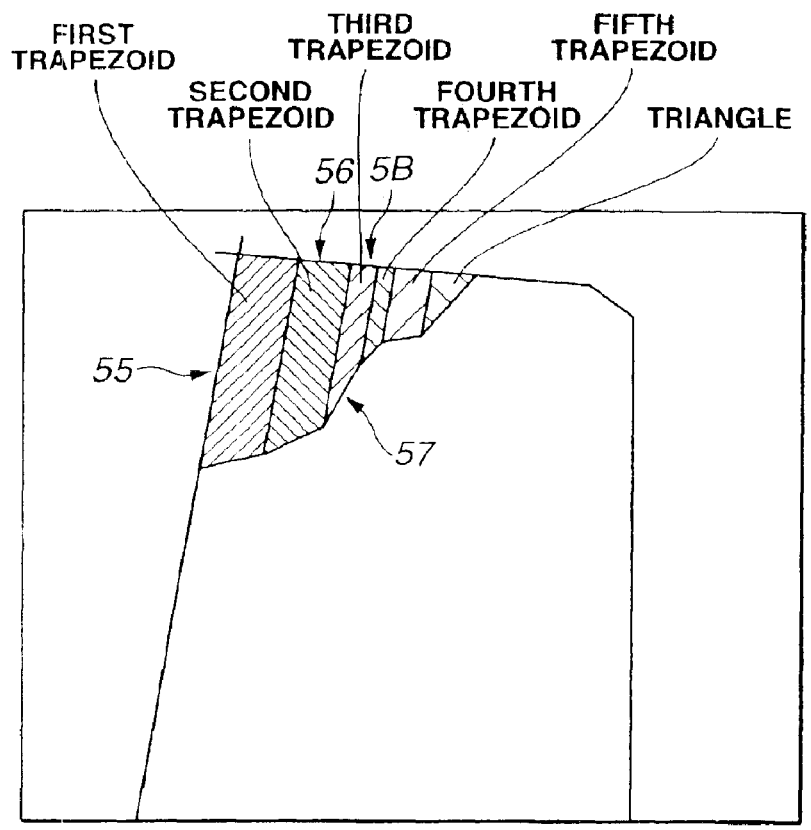
FIG. 11 is an explanatory diagram concerning a process of calculating the area of a missing edge portion.

The calculation of the area of the missing edge portion 53 is such that the missing portion is, as shown in FIG. 11, replaced with a manifold of a plurality of trapezoids (for example, first to fifth trapezoids) and one triangle, and the areas of the trapezoids and triangle are calculated and summated.

Referring to FIG. 12 to FIG. 19, a procedure of calculating the area of a missing edge portion will be detailed below.

First, the first procedure and the determination of the first reference line that accompanies the first procedure will be described below.

Figure 12:
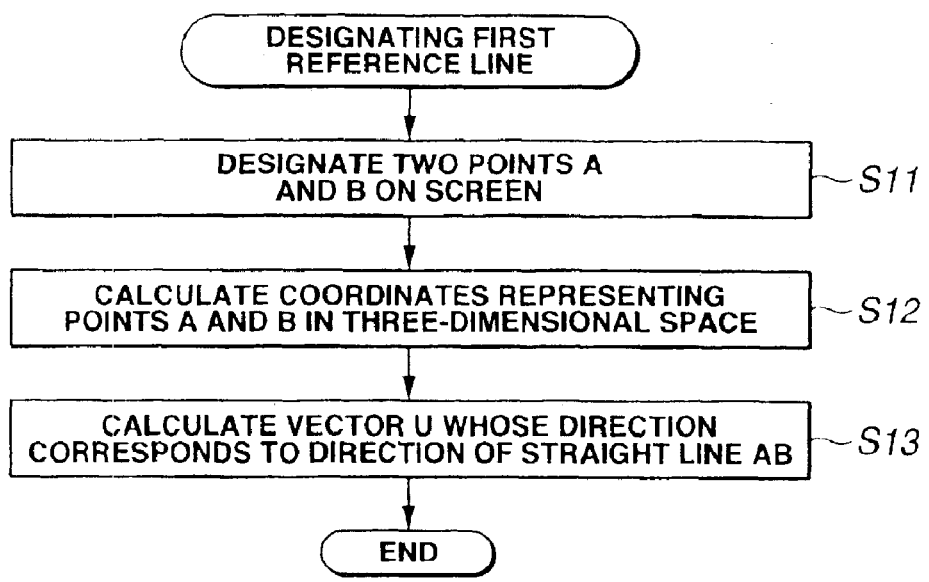
FIG. 12 is a flowchart describing a procedure of designating a first reference line.
Figure 13:
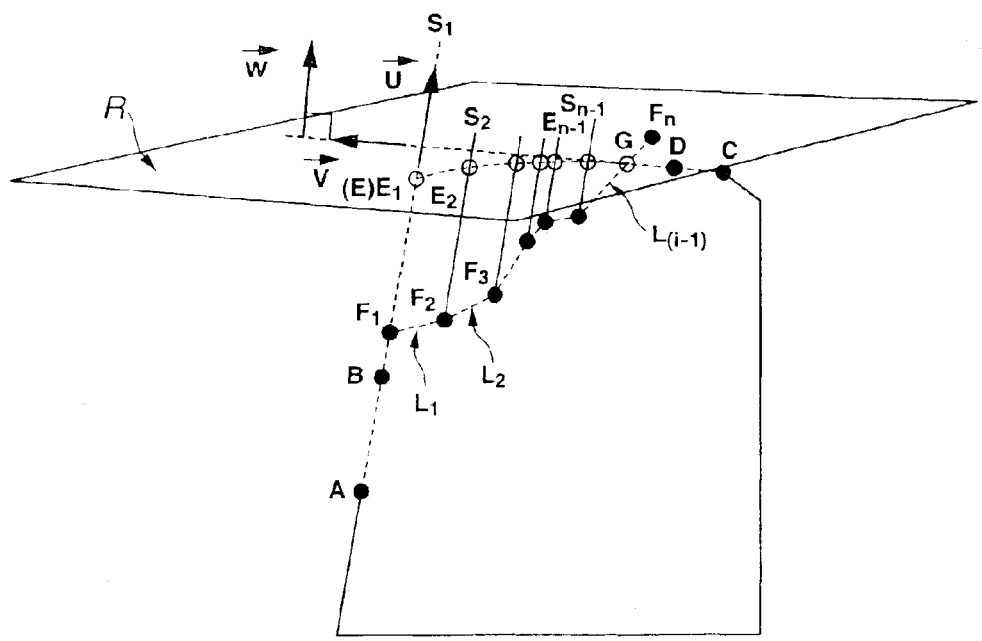
FIG. 13 is an explanatory diagram concerning the procedure and showing a screen.

An inspector designates two points A and B on the screen at step S11 described in FIG. 12 (see FIG. 13). At this time, the inspector handles the lever switch 42 on the remote controller 4 to designate the points.

When the points A and B are designated, the first reference line designation block 18c included in the missing-edge portion measurement block 18b calculates coordinates representing the points A and B in the three-dimensional space at step S12. At step S13, a direction vector U whose direction represents the direction of the straight line AB passing through the two points A and B is calculated. Consequently, the straight line AB is adopted as the first reference line 55 shown in FIG. 11.

Next, the second procedure and the determination of the first reference plane accompanying the second procedure will be described below.

Figure 15:
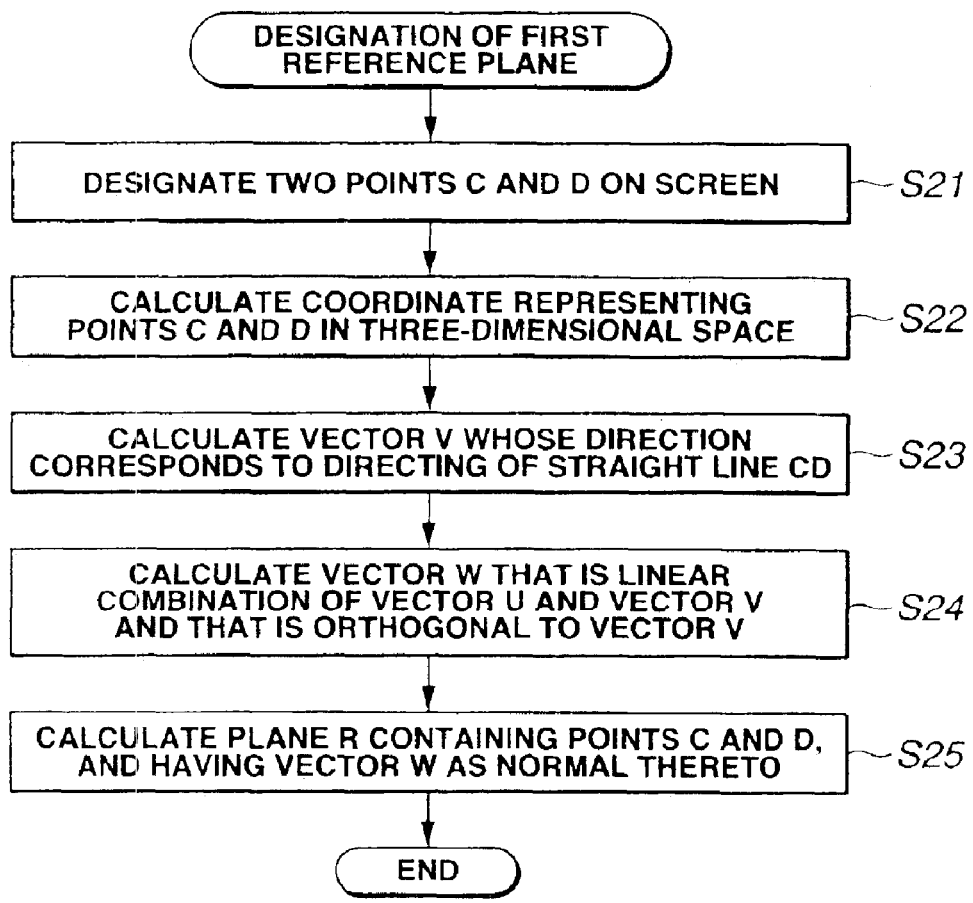
FIG. 15 is a flowchart describing a procedure of designating a first reference plane.

An inspector designates two points C and D, which are new points, on the screen at step S21 described in FIG. 15 (see FIG. 13). Specifically, the inspector handles the lever switch 42 on the remote controller 4 to designate the points.

When the points C and D are designated, the first reference plane designation block 18d included in the missing-edge portion measurement block 18b calculates coordinates, which represent the points C and D in the three-dimensional space, at step S22. At step S23, a straight line passing through the points C and D is adopted as the second reference line, and a direction vector V whose direction represents the direction of the second reference line is calculated (see FIG. 13 and FIG. 14).

Figure 14:
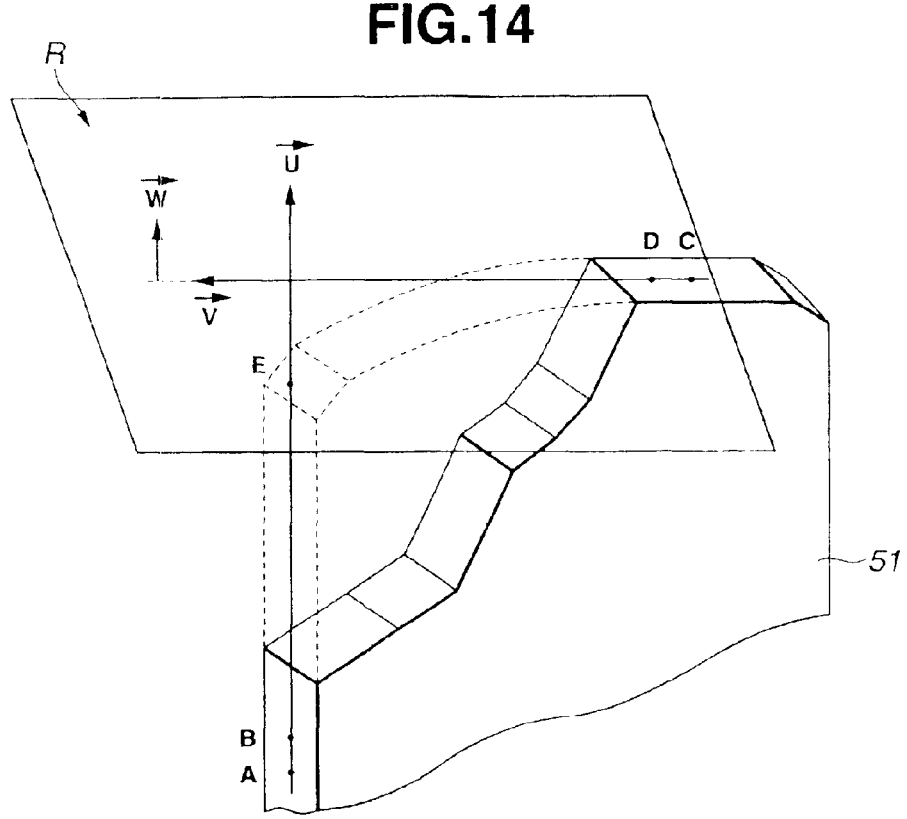
FIG. 14 is an explanatory diagram concerning the procedure and showing an actual curved blade.

At this time, since the turbine blade is the curved blade 51, the straight lines AB and CD generally have the positional relationship of not intersecting each other. At step S24, a vector that corresponds to a linear combination of the vectors U and V and that crosses the vector V at right angles is calculated as vector W as shown in FIG. 13 and FIG. 14.

Thereafter, control is passed to step S25. A plane containing the points C and D and having the vector W as a normal thereto is determined as plane R. Consequently, the plane R is adopted as the first reference plane 56 shown in FIG. 11. The plane R intersects the vector U at one point E.

Next, the third procedure and the determination of a missing-contour border accompanying the third procedure will be described below.

An inspector handles the lever switch 42 on the remote controller 4 so as to designate points F1, etc., and Fn for the purpose of determining the missing-contour border 57.

Figure 16:
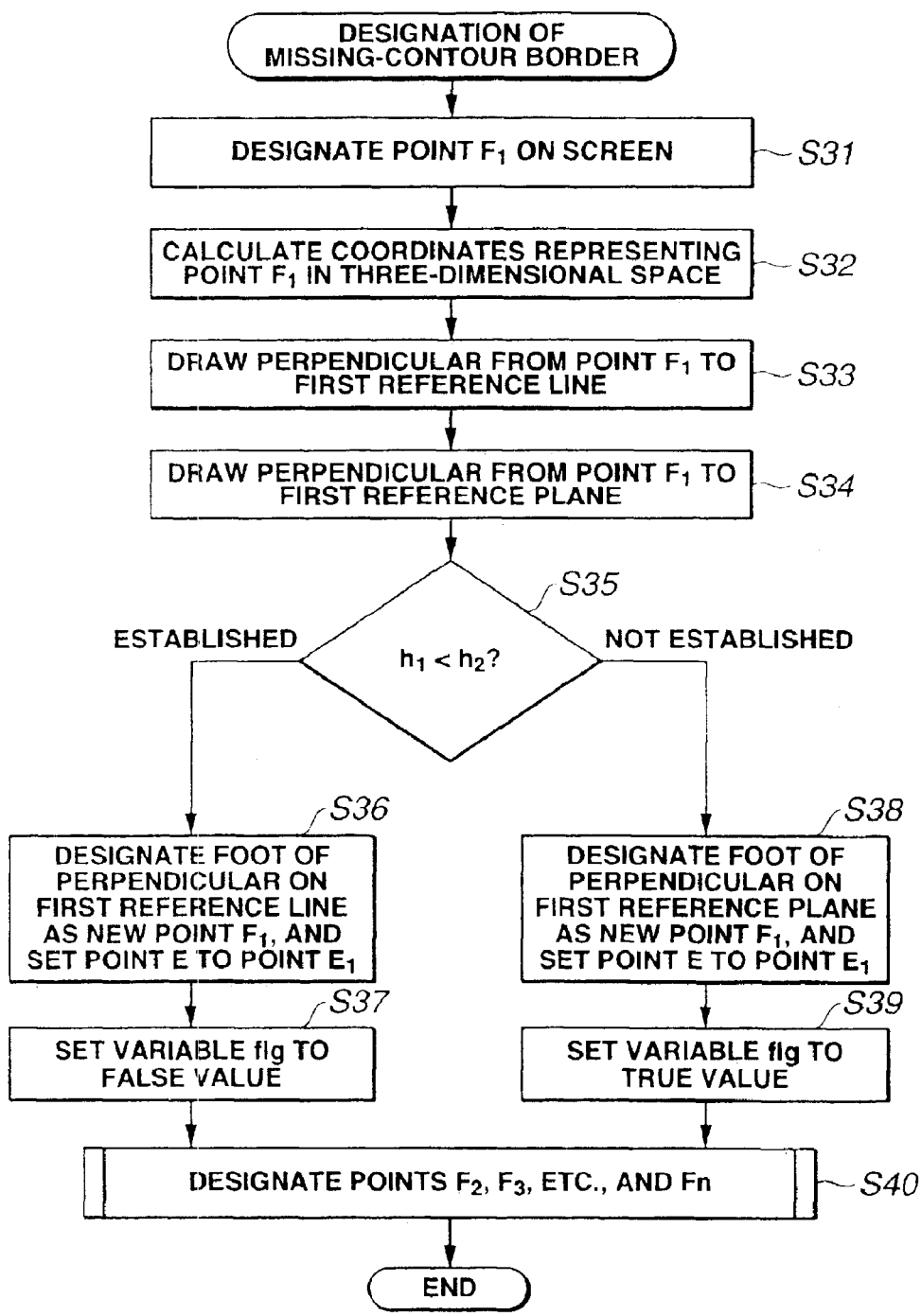
FIG. 16 is a flowchart describing a procedure of designating a missing-contour border.

First, at step S31 described in FIG. 16, the first point F1 is designated on the screen. At this time, the inspector designates the point F1 near the first reference line 55 as shown in FIG. 17A or near the first reference plane 56 as shown in FIG. 17B.

When the point F1 is designated near either the first reference line 55 or first reference plane 56, control is passed to step S32. Coordinates representing the point F1 in the three-dimensional space are calculated. Thereafter, it is verified whether the point F1 has the positional relationship shown in FIG. 17A or the positional relationship shown in FIG. 17B.

At step S33, a perpendicular is extended from the point F1 to the first reference line 55. The length of the perpendicular is calculated as length h1, and control is passed to step S34. At step S34, a perpendicular is extended from the point F1 to the first reference plane 56. The length of the perpendicular is calculated as length h2, and control is passed to step S35. At step S35, the length h1 is compared with the length h2.

When it is found at step S35 that the relationship of h1<h2 is established, it is verified that the point F1 is located near the first reference line 55. Control is then passed to step S36. At step S36, the foot of the perpendicular on the first reference line 55 is designated as new point F1, and point E1 is designated as new point E1. Control is then passed to step S37. A variable flg is set to a false value, and control is passed to step S40. The points F2, etc., and Fn are then designated.

On the other hand, when it is found at step S35 that the relationship of h1<h2 is not established, it is verified that the point F1 is located near the first reference plane 56. Control is then passed to step S38. At step S38, the foot of a perpendicular on the first reference plane 56 is designated as new point F1, and the point E is designated as new point E1. Control is then passed to step S39. The variable flg is set to a true value, and control is passed to step S40.

Figure 18:
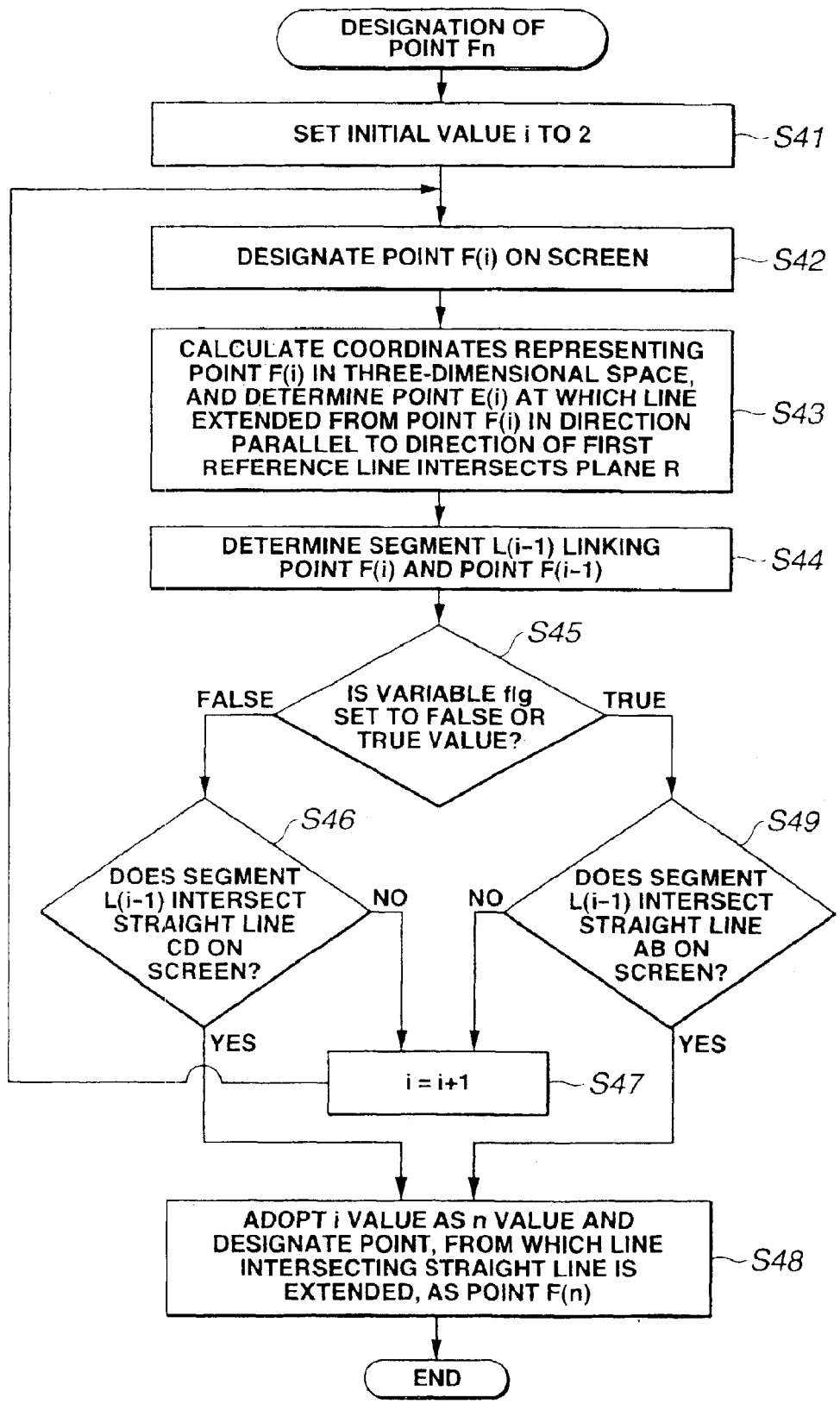
FIG. 18 is a flowchart describing a procedure of determining second and subsequent points so as to determine a contour border.

At step S41 described in FIG. 18, an initial value i is set to 2 so that a point F(i) (that is, point F2, etc., or point Fn) will be designated sequentially. Thereafter, the points succeeding the point F1 are designated. At step S42, the point F(i) is designated on the screen.

When the point F(i) is designated, control is passed to step S43. Coordinates representing the point F(i) in the three-dimensional space are calculated. Moreover, the point F(i) is moved in a direction parallel to the direction of the first reference line 55, whereby point E(i) that is a point of intersections at which the trace of the point F(i) intersects the first reference plane 56 is determined. Control is then passed to step S44.

At step S44, a segment L(i−1) linking the point F(i) and point F(i−1) is determined: At step S45, it is checked whether the variable flg is set to the false value or the true value. When it is found at step S45 that the variable flg is set to the false value, control is passed to step S46. It is then verified whether the segment L(i−1) intersects the straight line CD on the screen.

When it is found at step S46 that the segment L(i−1) does not intersect the straight line CD on the screen, the value i is incremented by 1 at step S47. Control is returned to step S42, and the next point F(i+1) is designated on the screen.

When it is verified at step S46 that the segment L(i−1) intersects the straight line CD on the screen, control is passed to step S48. The point of intersection is defined as point G. The work of designating the point F(i) is terminated. The value i adopted at that time is designated as value n, and the point G is designated as point Fn.

On the other hand, when it is verified at step S45 that the variable flg is set to the true value, control is passed to step S49. It is verified whether the segment L(i−1) intersects the straight line AB on the screen. When it is verified at step S49 that the segment L(i−1) does not intersect the straight line AB on the screen, control is passed to step S47. The value i is incremented by 1, and control is returned to step S42. The next point F(i+1) is then designated on the screen.

When it is verified at step S49 that the segment L(i−1) intersects the straight line AB on the screen, control is passed to step S47. The point of intersection is defined as point G, and the work of designating the point F(i) is terminated. The value i adopted at that time is designated as the value n and the point G is designated as the point Fn.

A polygonal line formed with successive segments L1, L2, etc., and L(i−1) is adopted as the missing-contour border 57.

Finally, calculation of the area of a missing edge portion will be described below.

When an inspector has achieved the foregoing procedures, the points E1, etc., and E(i−1) contained in the first reference plane 56 as shown in FIG. 13 and the points F1, etc., and F(i−1) defining the missing-contour border 57 and the point G are determined. Consequently, the arithmetic and logic block 18f calculates the area of the missing edge portion on the basis of the coordinates representing the points in the three-dimensional space according to the procedure described below.

Figure 19:
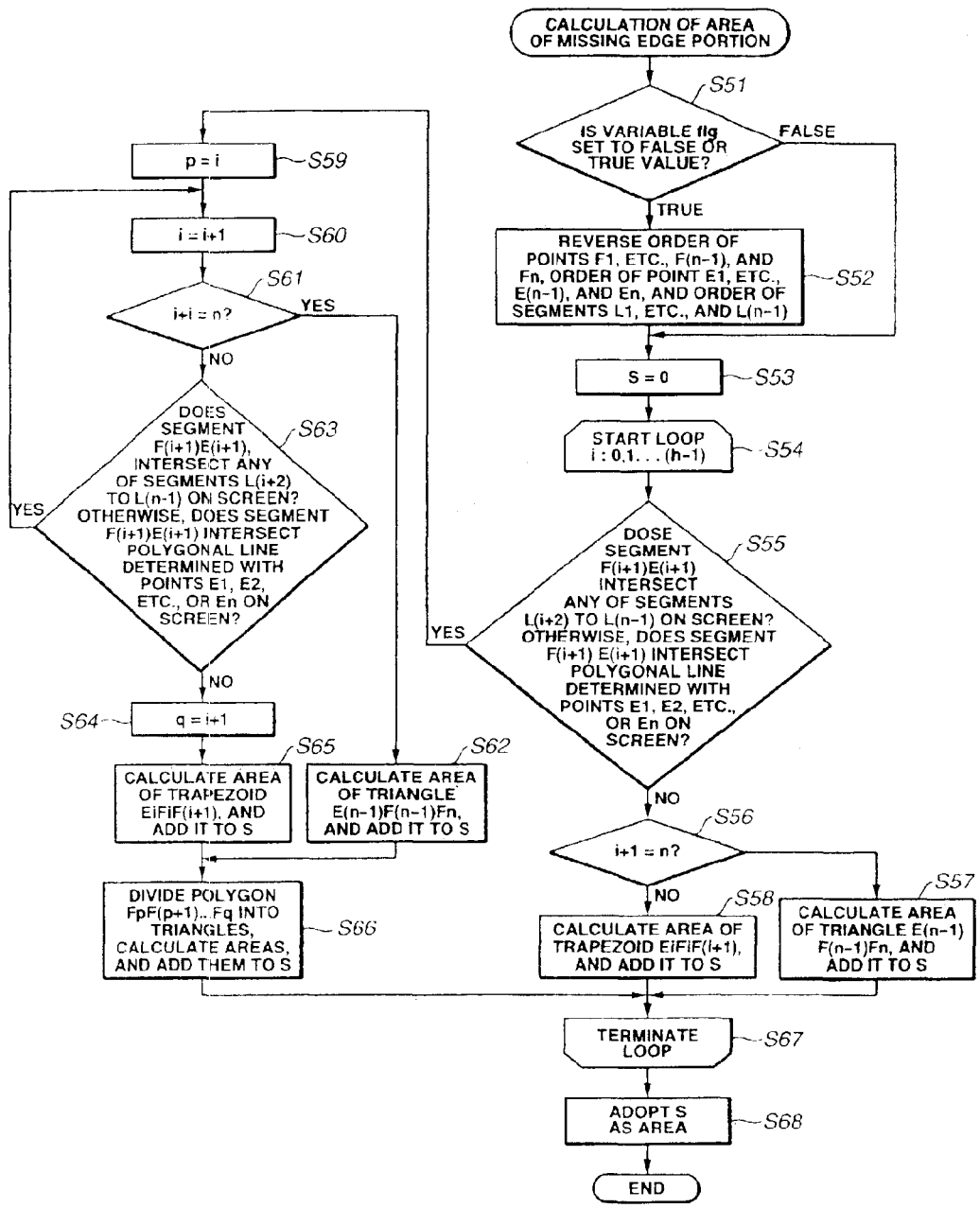
FIG. 19 is a flowchart describing a process of calculating the area of a missing edge portion.

First, it is checked at step S51 described in FIG. 19 whether the variable flg is set to the false or true value. When it is confirmed at step S51 that the variable flg is set to the false value, control is passed to step S53. The area of the missing edge portion is then calculated. On the other hand, when it is confirmed that the variable flg is set to the true value at step S51, all the points F1 to Fn and points E1 to En that are determined orderly from the first reference plane 56 side as shown in FIG. 17B are rearranged reversely. Namely, the point F1 determined first is re-designated as point Fn, and the point Fn determined last is re-designated as point F1. Likewise, the point E1 is re-designated as point En, and the point En is re-designated as point E1. Control is then passed to step S53.

Owing to the re-designation of the points, the locations of the points are identical to those shown in FIG. 13 and FIG.

17A. At this time, the points Fn, En, and G share the same point. Moreover, the segments L1 to L(i−1) are also rearranged reversely.

Referring to steps S53 to S68, the procedure of calculating the area of a missing edge portion will be described below.

First, at step S53, the variable S of an area is initialized. Area calculation is then performed within the loop from step S54 to step S67. First, at step S54, a variable i is initialized to 0, an increment is set to 1, and an end value is set to n−1. The loop is then started.

At step S55, it is verified whether segment F(i+1)E(i+1) intersects any of the segments L(i+2) to L(n−1) on the screen, or whether the segment F(i+1)E(i+1) intersects a polygonal line formed with the points E1, E2, etc., and En on the screen.

When the segment F(i+1)E(i+1) intersects neither any of the segments L(i+2) to L(n−1 nor the polygonal line, control is passed to step S56. It is then verified whether value i+1 equals the value n. When the value i+1 does not equal the value n, the area of trapezoid EiFiF(i+1)E(i+1) is calculated at step S58, and added to the variable S. When the value i+1 equals the value n, the area of triangle E(n−1)F(n−1)Fn is calculated and added to the variable S.

On the other hand, when the criteria of step S55 are met, it is decided that the shape of the field is too complex to calculate the area thereof by dividing the field into trapezoids. Control is then returned to step S59.

At step S59, the value i adopted at that time is preserved as variable p. At step S60, the value i is incremented by 1. At step S61, it is verified whether the value i+1 equals the value n. When the value i+1 does not equal the value n, control is passed to step S63. The same verification as the one of step S55 is then performed. When either of the criteria is met at step S63, control is returned to step S59. The processing is performed repeatedly. In other words, the value i is kept incremented until neither criteria of step S63 is met.

When neither criteria of step S63 is met, control is passed to step S64 and the value i adopted at that time is preserved as a variable q. Control is then passed to step S65. The area of trapezoid EpFpFqEq is calculated and added to the variable S. Control is then passed to step S66. When it is verified at step S61 that the value i+1 equals the value n, the same processing as that of step S57 is performed at step S62. Control is then passed to step S66.

At step S66, polygon FqF(p+1) . . . Fq is divided into triangles, and the areas of the triangles are calculated and added to the variable S. Thereafter, control is returned to a step that is included in the loop and that precedes step S67.

After the loop is terminated, the variable S is adopted as the missing area at step S68. Thus, the calculation of the area of a missing edge portion is completed.

As mentioned above, when a portion of an edge is found missing, an inspector performs on the screen of the monitor the work of designating the first reference line, the work of designating the first reference plane, and the work of designating the missing-contour border. This causes the missing edge portion measurement block to perform predetermined arithmetic and logic operations. Consequently, the area of the missing edge portion can be calculated easily and smoothly.

Figure 20:
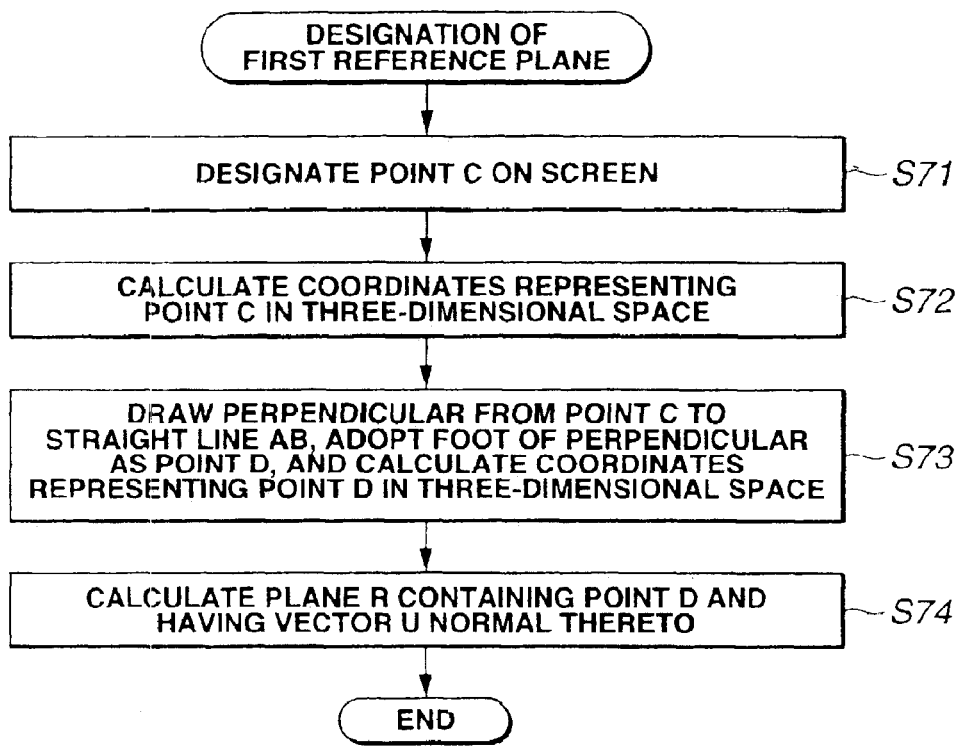
FIG. 20 is a flowchart describing a process of designating a first reference plane of a block blade.

When a portion of an edge of the block blade 52 shown in FIG. 7B is found missing, only the procedure for designating the first reference plane is modified as described in the flowchart of FIG. 20. The other procedures are identical to those described in FIG. 10.

Figure 21:
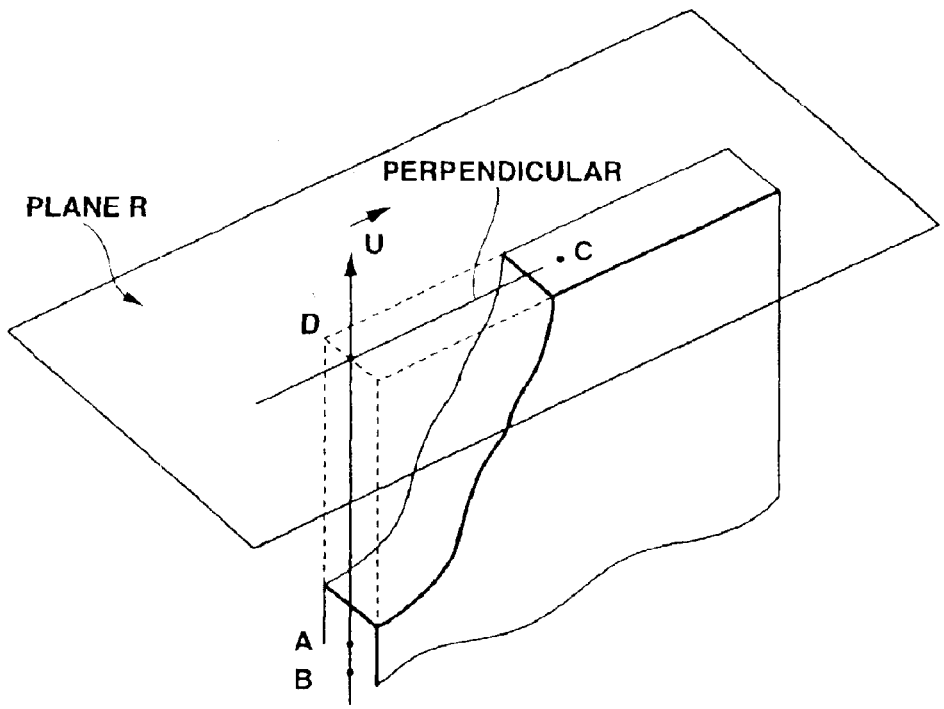
FIG. 21 is an explanatory diagram concerning the procedure described in FIG. 20 and showing an actual block blade.

In the case of the block blade 52, one point C is designated on the screen at step S71. At step S72, coordinates representing the point C in the three-dimensional space are then calculated. Thereafter, at step S73, a perpendicular is extended from the point C to the straight line AB. The foot of the perpendicular is defined as point D, and coordinates representing the point D in the three-dimensional space are calculated. At step S74, a plane containing the point D and having the vector U as a normal thereto is determined. Consequently, the plane is, similarly to the plane R, adopted as the first reference plane as shown in FIG. 21.

As mentioned above, since the block blade is shaped substantially like a rectangular parallelepiped, when the first reference plane is designated, only one point C should be designated on the screen. The first reference plane having the vector U, of which direction represents the direction of the first reference line, as a normal thereto is then determined. Consequently, the area of the missing edge portion can be calculated easily and smoothly in the same manner as that in the aforesaid embodiment.

The preferred embodiments of the present invention have been described with reference to the accompanying drawings. It should be understood that the present invention is not limited to the precise embodiments but any skilled person in the art can make various changes and modifications without departing from the spirit or scope of the invention defined in the appended claims.

What is claimed is:

1. A measurement endoscope system comprising:

an electronic endoscope having an imaging unit;

an image processing unit for receiving an imaging signal from the imaging unit and producing a video signal;

a control device including at least a control unit that has a measurement processing block which performs measurement processing on the basis of an image signal produced by the image processing unit; and a display device for receiving a video signal transmitted in response to a direction given by the control unit included in the control device, and displaying an image represented by the video signal, wherein:

the measurement processing block included in the control unit has a missing-edge portion measuring means for measuring the area of a missing portion of an edge of an object matter; and the missing-edge portion measuring means comprises:

a first reference line designating means for designating a first reference line that corresponds to a side surface of the object matter which the periphery of the missing edge portion used to contain;

a first reference plane designating means for designating a first reference plane that corresponds to the top of the object matter which the periphery of the missing edge used to contain, and that intersects the first reference line, which is designated by the first reference line designating means, at one point;

a contour designating means for determining a missing-contour border by designating any points on the border of the missing edge portion; and an arithmetic and logic means for calculating the area of a field that is formed by moving the missing-contour border, which is designated by the contour designating means, up to the first reference plane in a direction parallel to the direction of the first reference line, and that is defined with the missing-contour border, first reference line, and first reference plane.

2. A measurement endoscope system according to claim 1, wherein:

the first reference plane is a plane containing a second reference line that passes through two points which are contained in the top of the object matter and which are located near the missing portion; and a vector normal to the first reference plane, that is, a direction vector whose direction represents the direction of the first reference line, and a direction vector whose direction represents the direction of the second reference line are contained in the same plane.

3. A measurement endoscope system according to claim 1, wherein the first reference plane is a plane passing through one point that is contained in the top of the object matter and that is located near the missing portion, and the vector normal to the first reference plane corresponds to the direction vector whose direction represents the direction of the first reference line.

4. A measurement endoscope system according to claim 2, wherein the missing-contour border is approximated to a polygonal line formed by linking n points where n denotes 2 or more.

5. A measurement endoscope system according to claim 3, wherein the missing-contour border is approximated to a polygonal line formed by linking n points where n denotes 2 or more.

6. A measurement endoscope system according to claim 4, wherein the area is calculated as the sum of the area of one triangle and the areas of (n–2) trapezoids.

7. A measurement endoscope system according to claim 5, wherein the area is calculated as the sum of the area of one triangle and the areas of (n–2) trapezoids.

8. A measurement endoscope system according to claim 1, further comprising a plurality of types of optical adapters freely detachably attached to the distal section of the electronic endoscope and each provided with a predetermined observational optical system.

* * * * *